United States Patent
Jeon et al.

(10) Patent No.: US 9,354,187 B2
(45) Date of Patent: May 31, 2016

(54) APPARATUS AND METHOD FOR COMPUTED TOMOGRAPHY IMAGE PROCESSING

(71) Applicant: INSTITUTE FOR BASIC SCIENCE, Daejeon (KR)

(72) Inventors: Ki Wan Jeon, Daejeon (KR); Chi Young Ahn, Daejeon (KR); Sung Whan Kim, Daejeon (KR)

(73) Assignee: INSTITUTE FOR BASIC SCIENCE (KR)

(*) Notice: Subject to any disclaimer, the term of this patent is extended or adjusted under 35 U.S.C. 154(b) by 0 days.

(21) Appl. No.: 14/538,150

(22) Filed: Nov. 11, 2014

(65) Prior Publication Data
US 2015/0212015 A1 Jul. 30, 2015

(30) Foreign Application Priority Data
Jan. 24, 2014 (KR) .................. 10-2014-0009036

(51) Int. Cl.
G06K 9/00 (2006.01)
G01N 23/04 (2006.01)
G06T 11/00 (2006.01)

(52) U.S. Cl.
CPC ............ *G01N 23/046* (2013.01); *G06T 11/003* (2013.01)

(58) Field of Classification Search
CPC .................... G01N 23/046; G06T 11/003
See application file for complete search history.

(56) References Cited

U.S. PATENT DOCUMENTS

| | | | | |
|---|---|---|---|---|
| 3,965,358 A * | 6/1976 | Macovski | ............ | G01N 23/083 378/157 |
| 4,029,963 A * | 6/1977 | Alvarez | ............ | A61B 6/032 250/360.1 |
| 4,433,380 A * | 2/1984 | Abele | ............ | A61B 6/032 378/901 |
| 5,937,102 A * | 8/1999 | Jin | ............ | G06T 11/006 382/131 |
| 6,973,158 B2 * | 12/2005 | Besson | ............ | A61B 6/508 378/16 |
| 7,197,172 B1 * | 3/2007 | Naidu | ............ | G01N 23/227 378/62 |

(Continued)

FOREIGN PATENT DOCUMENTS

KR 10-2001-0006602 A 1/2001

OTHER PUBLICATIONS

Alvarez, Robert E. "Near optimal energy selective x-ray imaging system performance with simple detectors." Medical physics 37.2 (2010): 822-841.*

*Primary Examiner* — Stephen R Koziol
*Assistant Examiner* — Jonathan S Lee
(74) *Attorney, Agent, or Firm* — Schmeiser, Olsen & Watts, LLP

(57) ABSTRACT

An apparatus and method for computed tomography image processing is provided. The apparatus includes: an X-ray detection unit that detects an X-ray beam having passed through a subject and outputs an energy value thereof; a line integral calculation unit that calculates line integral values of attenuation coefficients representing attenuation of the energy value of the X-ray beam having passed through the subject and been detected, based on the energy value; an image processing unit that reconstructs a tomogram based on the line integral values; and an image output unit that outputs the tomogram. The apparatus and method for computed tomography image processing can calculate line integral values of attenuation coefficients constituting an integrand of an X-ray projection function using the mean value theorem for integrals in order to restore an image of a subject from an X-ray beam detected in computed tomography image processing.

8 Claims, 2 Drawing Sheets

(56) References Cited

U.S. PATENT DOCUMENTS

Figure 1:
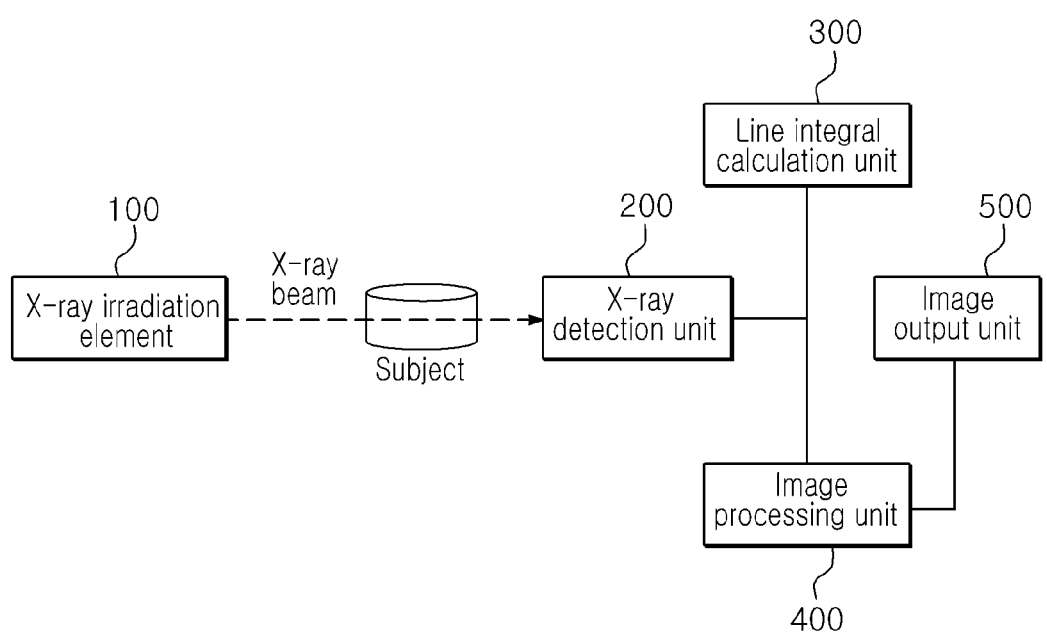

| | | | |
|---|---|---|---|
| 8,818,065 B2 * | 8/2014 | Yang | G06T 11/005 382/131 |
| 2003/0156684 A1 * | 8/2003 | Fessler | A61B 6/032 378/210 |
| 2004/0022348 A1 * | 2/2004 | Heumann | G01N 23/046 378/4 |
| 2008/0187091 A1 * | 8/2008 | Basu | G01N 23/046 378/5 |
| 2009/0262997 A1 * | 10/2009 | Zou | G06T 11/005 382/131 |

* cited by examiner

APPARATUS AND METHOD FOR COMPUTED TOMOGRAPHY IMAGE PROCESSING

CROSS-REFERENCE TO RELATED APPLICATIONS

This application claims priority to KR10-2014-0009036, having a filing date of Jan. 24, 2014, the entire contents of which are hereby incorporated by reference.

FIELD OF TECHNOLOGY

The following relates to an apparatus and method for computed tomography image processing, and more particularly, to an apparatus and method for computed tomography image processing which can calculate line integral values of attenuation coefficients constituting an integrand of an X-ray projection function using the mean value theorem for integrals in order to restore an image of a subject from an X-ray beam detected in computed tomography image processing.

BACKGROUND

In order to restore a computed tomogram, measurements of X-ray beams passing through a subject are reduced into a line integral, which in turn is inversely transformed into a projection function which represents attenuation coefficients of the subject.

Although monochromatic irradiation is required to obtain accurate values, all tomography instruments in the related art employ multi-chromatic irradiation in practice. Since tomograms reconstructed by multi-chromatic irradiation include strong artifacts, it is very difficult to calculate accurate line integrals of attenuation coefficients and to obtain accurate values of nonlinear problems provided by inverse transformation of an X-ray projection function.

A solution to such artifacts can be obtained by dual-energy tomography. In dual-energy tomography, the same subject is subjected to bi-chromatic irradiation with different energy levels. Images obtained through dual-energy tomography include fewer beam hardening artifacts.

An X-ray projection function of two spectra by dual-energy tomography is represented by simultaneous line integral equations of attenuation coefficients, and the measurements of X-ray beams detected in the two different spectra are substituted into the simultaneous equation to obtain line integral values.

These simultaneous equations are nonlinear equations as mentioned above, and polynomial approximation is generally used to solve the nonlinear equations. However, polynomial approximation doesn't provide accurate values of the equations. Moreover, it is also problematic in that irradiation and measurements of X-ray beams for calibration are required several times to obtain coefficients of the polynomials.

One example of the related art is disclosed in Korean Patent Publication No. 10-2001-0006602 (Publication date: Jan. 26, 2001) entitled "Apparatus and method for computed tomography".

SUMMARY

Embodiments of the present invention provide an apparatus and method for computed tomography image processing, which can calculate line integral values of attenuation coefficients constituting an integrand of an X-ray projection function using the mean value theorem for integrals in order to restore an image of a subject from an X-ray beam detected in computed tomography image processing, thereby enabling efficient removal of artifacts from an X-ray tomogram while improving accuracy of the image.

In accordance with one aspect of an embodiment of the present invention, an apparatus for computed tomography image processing includes: an X-ray detection unit that detects an X-ray beam having passed through a subject and outputs an energy value thereof; a line integral calculation unit that calculates line integral values of attenuation coefficients representing attenuation of the energy value of the X-ray beam having passed through the subject and detected, based on the energy value; an image processing unit that reconstructs a tomogram based on the line integral values; and an image output unit that outputs the tomogram, wherein the line integral calculation unit calculates, based on simultaneous equations obtained from a projection function of two different energy spectra and the energy value of the detected X-ray beam, line integral values of attenuation coefficients included in the projection function of the two different energy spectra and energy values satisfying the simultaneous equations.

The line integral calculation unit may calculate approximate values of the energy values satisfying the simultaneous equations based on first approximate values of the line integral values of the attenuation coefficients, and calculate second approximate values of the line integral values of the attenuation coefficients based on the approximate values of the energy values satisfying the simultaneous equations.

Initial approximate values of the energy values satisfying the simultaneous equations may be mean values of energy values of the two different energy spectra, respectively.

The line integral calculation unit may calculate the line integral values of the attenuation coefficients and the approximate values of the energy values satisfying the simultaneous equations when differences between the first and second approximate values of the line integral values of the attenuation coefficients are less than or equal to preset limits.

The line integral calculation unit may replace the first approximate values of the line integral values of the attenuation coefficients with the second approximate values of the line integral values of the attenuation coefficients, and repeat a procedure of calculating the approximate values of the energy values satisfying the simultaneous equations and the second approximate values of the line integral values of the attenuation coefficients, when the differences between the first approximate values and the second approximate values of the line integral values of the attenuation coefficients exceed the preset limits.

The line integral calculation unit may select the lowest energy values as the approximate values of the energy values satisfying the simultaneous equations, among energy values satisfying an equation in which the line integral values of the attenuation values in the simultaneous equations are replaced by the first approximate values of the line integral values of the attenuation values.

The line integral calculation unit may select the highest energy values as the approximate values of the energy values satisfying the simultaneous equations, among energy values satisfying an equation in which the line integral values of the attenuation values in the simultaneous equations are replaced by the first approximate values of the line integral values of the attenuation values.

The line integral calculation unit may determine the energy values satisfying the simultaneous equations as functions of two variables with respect to pairs of real numbers that can be differentiated at an original point, and select the approximate values of the energy values satisfying the simultaneous equations through approximation.

In accordance with another aspect of an embodiment of the present invention, a method for computed tomography image processing includes: detecting, by an X-ray detection unit, an X-ray beam emitted to a subject and outputting an energy value thereof; calculating, by a line integral calculation unit, line integral values of attenuation coefficients representing attenuation of the energy value of the X-ray beam having passed through the subject and detected, based on the energy value; reconstructing, by an image processing unit, a tomogram based on the line integral values; and outputting, by an image output unit, the tomogram, wherein the line integral calculation unit calculates, based on simultaneous equations obtained from a projection function of two different energy spectra and the energy value of the detected X-ray beam, line integral values of attenuation coefficients included in the projection function of the two different energy spectra and energy values satisfying the simultaneous equations.

Calculating, by the line integral calculation unit, line integral values of attenuation coefficients may include: calculating approximate values of the energy values satisfying the simultaneous equations based on first approximate values of the line integral values of the attenuation coefficients; and calculating second approximate values of the line integral values of the attenuation coefficients based on the approximate values of the energy values satisfying the simultaneous equations.

The method may further include initializing, by the line integral calculation unit, the approximate values of the energy values satisfying the simultaneous equations as mean values of energy values of the two different energy spectra, respectively.

Calculating, by the line integral calculation unit, line integral values of attenuation coefficients may include: calculating the line integral values of the attenuation coefficients and the approximate values of the energy values satisfying the simultaneous equations when differences between the first and second approximate values of the line integral values of the attenuation coefficients are less than or equal to preset limits.

Calculating, by the line integral calculation unit, line integral values of attenuation coefficients may include: repeating a procedure of calculating the approximate values of the energy values satisfying the simultaneous equations and the second approximate values of the line integral values of the attenuation coefficients, when the differences between the first approximate values and the second approximate values of the line integral values of the attenuation coefficients exceed the preset limits.

In calculation of the approximate values of the energy values satisfying the simultaneous equations, the line integral calculation unit may select the lowest energy values as the approximate values of the energy values satisfying the simultaneous equations, among energy values satisfying an equation in which the line integral values of the attenuation values in the simultaneous equations are replaced by the first approximate values of the line integral values of the attenuation values.

In calculation of the approximate values of the energy values satisfying the simultaneous equations, the line integral calculation unit may select the highest energy values as the approximate values of the energy values satisfying the simultaneous equations, among energy values satisfying an equation in which the line integral values of the attenuation values in the simultaneous equations are replaced by the first approximate values of the line integral values of the attenuation values.

In calculation of the approximate values of the energy values satisfying the simultaneous equations, the line integral calculation unit may determine the energy values satisfying the simultaneous equations as functions of two variables with respect to pairs of real numbers that can be differentiated at an original point, and select the approximate values of the energy values satisfying the simultaneous equations through approximation for calculating values of the functions of two variables with respect to the first approximate values of the attenuation coefficients.

According to an embodiment of the present invention, the apparatus and method for processing a tomogram can calculate line integral values of attenuation coefficients constituting an integrand of an X-ray projection function using the mean value theorem for integrals in order to restore an image of a subject from an X-ray beam detected in computed tomography image processing, thereby enabling efficient removal of artifacts from an X-ray tomogram while improving accuracy of the image through single X-ray irradiation without additional correction and repeated X-ray irradiation.

BRIEF DESCRIPTION

Figure 2:
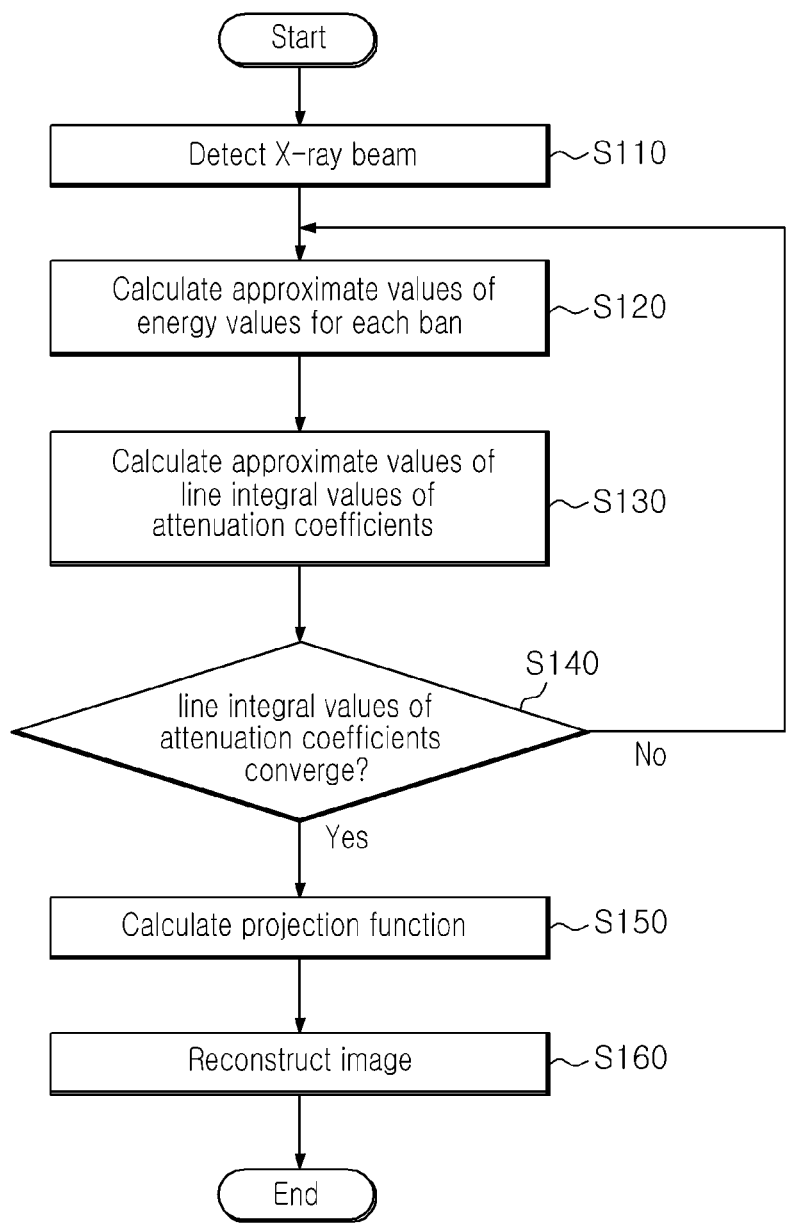

Some of the embodiments will be described in detail, with reference to the following figures, wherein like designations denote like members, wherein:

FIG. 1 is a diagram of an apparatus for computed tomography image processing in accordance with one embodiment of the present invention; and FIG. 2 is a flowchart illustrating a method for computed tomography image processing in accordance with one embodiment of the present invention.

DETAILED DESCRIPTION

Hereinafter, exemplary embodiments of the present invention will be described in detail with reference to the accompanying drawings. It should be noted that the drawings are not to precise scale and may be exaggerated in thickness of lines or size of components for descriptive convenience and clarity. In addition, the terms used herein are defined by taking functions of the present embodiments of the invention into account and can be changed according to user or operator custom or intention. Therefore, definition of the terms should be made according to the overall disclosure set forth herein.

FIG. 1 is a diagram of an apparatus for computed tomography image processing in accordance with one embodiment of the present invention.

Referring to FIG. 1, the apparatus for computed tomography image processing according to the embodiment of the invention may include an X-ray detection unit 200, a line integral calculation unit 300, an image processing unit 400, and an image output unit 500.

The X-ray detection unit 200 detects an X-ray beam emitted from an X-ray irradiation unit 100 and having passed through a subject, and outputs an energy value of the X-ray beam.

The line integral calculation unit 300 calculates, based on the energy value of the output X-ray beam, line integral values of attenuation coefficients which represent attenuation of the energy value of the X-ray beam having passed through the subject and been detected. Here, the line integral calculation unit 300 calculates the line integral values of the attenuation coefficients by solving simultaneous equations of a projection function obtained through irradiation of an X-ray beam twice.

In X-ray tomography, X-ray beams having passed through a subject attenuate until the X-ray detection unit detects the X-ray beams. Thus, energy values of the X-ray beams detected after attenuation can be represented by the energy values of the X-ray beams having passed through the subject, which are substituted into the projection function.

The projection function of the X-ray beam is represented by Equation 1.

$$p = -\ln \int_I S(E) \exp[-\int_l \mu(r,E) ds] dE, \qquad \text{<Equation 1>}$$

In Equation 1, p represents an energy value of an X-ray beam, E represents photon energy of the X-ray beam, S represents a spectrum of energy distribution, I represents an integration zone of the photon energy of the X-ray beam, r represents a position vector of a path along which the X-ray beams travel, l represents the path along which the X-ray beams travel, and $\mu$ represents an attenuation coefficient of the X-ray beam.

In other words, $\int \mu(r,E) ds$ is a line integral which represents attenuation of an X-ray beam depending upon the path along which the X-ray beams travel.

It is known that the attenuation coefficient of the X-ray beam can be approximated by a linear combination of attenuations of the Compton effect and photoelectron interaction. The projection function of the X-ray beam to which the approximate attenuation coefficient is applied is provided by Equation 2.

$$p \approx -\ln \int_I S(E) \exp[-A_c f_{KN}(E) - A_p f_p(E)] dE$$

$$A_c = \int_l \alpha_c(r) ds, \quad A_p = \int_l \alpha_p(r) ds \qquad \text{<Equation 2>}$$

In Equation 2, $f_p$ represents energy dependency of photoelectric absorption, $f_{KN}$ represents Compton scattering effect, $a_c$ represents an attenuation coefficient by the Compton effect, and $a_p$ represents an attenuation coefficient by photoelectric absorption. $A_c$ and $A_p$ are line integral values of $a_c$ and $a_p$ for the path of the x-ray beam. Thus, $a_c$ and $a_p$, that is, the attenuation coefficients, can be calculated by obtaining the values of $A_c$ and $A_p$.

In order to obtain the line integral values of the two attenuation coefficients, the energy values of the X-ray beam in two energy spectra are detected and substituted into Equation 2 to establish simultaneous equations. These simultaneous equations are represented by Equation 3.

$$p_L \approx -\ln \int_I S_L(E) \exp[-A_c f_{KN}(E) - A_p f_p(E)] dE$$

$$p_H \approx -\ln \int_I S_H(E) \exp[-A_c f_{KN}(E) - A_p f_p(E)] dE \qquad \text{<Equation 3>}$$

In Equation 3, $P_L$ represents an energy value of an X-ray beam measured with respect to a low energy spectrum, $P_H$ represents an energy value of the X-ray beam measured with respect to a high energy spectrum, $S_L$ represents the low energy spectrum, and $S_H$ represents the high energy spectrum.

For instance, the entire spectrum of the X-ray beam may be in the range of 30 keV to 200 keV, the low energy spectrum may be in the range of 30 keV to 50 keV, and the high energy spectrum may be in the range of 70 keV to 120 keV.

The attenuation coefficients $a_c$ and $a_p$ can be calculated from the line integral values $A_c$ and $A_p$ of the attenuation coefficients obtained by solving Equation 3.

On the other hand, according to the mean value theorem for integrals, in the case where S, $f_{KN}$, and $f_p$ are consecutive, there is an energy value capable of providing the same value as a value obtained by dividing the integral term of Equation 2 by |I| when a certain energy value is applied to an integrand of Equation 2.

In other words, an energy value $E^{MV}$ satisfying Equation 4 is present.

$$-\ln \frac{1}{|I|} \int_I S(E) \exp[-A_c f_{KN}(E) - A_p f_p(E)] dE = \qquad \text{<Equation 4>}$$
$$-\ln S(E^{MV}) + A_c f_{KN}(E^{MV}) + A_p f_p(E^{MV})$$

Then, the following Equation 5 is obtained by substituting Equation 4 into equations corresponding to the high and low energy spectra in Equation 3.

$$-\ln\left(\frac{P_L}{|I|}\right) \approx -\ln S_L(E_L^{MV}) + A_c f_{KN}(E_L^{MV}) + A_p f_p(E_L^{MV}) \qquad \text{<Equation 5>}$$

$$-\ln\left(\frac{P_H}{|I|}\right) \approx -\ln S_H(E_H^{MV}) + A_c f_{KN}(E_H^{MV}) + A_p f_p(E_H^{MV})$$

The attenuation coefficients $a_c$ and $a_p$ can be calculated from the line integral values $A_c$ and $A_p$ of the attenuation coefficients obtained by solving Equation 5.

Here, energy values $E_L^{MV}$ and $E_H^{MV}$, the existence of which is guaranteed by the mean value theorem for integrals, depend upon the line integral values $A_c$ and $A_p$ of the attenuation coefficients. Consequently, $E_L^{MV}$ and $E_H^{MV}$ can be considered as a set of real numbers in a set of pairs of real numbers.

In addition, since the existence of the energy values $E_L^{MV}$ and $E_H^{MV}$ is guaranteed by the mean value theorem for integrals, the energy values can be obtained by repeatedly obtaining approximate values thereof until the approximate values converge.

As such, the line integral calculation unit 300 calculates the attenuation coefficients $a_c$ and $a_p$ and the energy values $E_L^{MV}$ and $E_H^{MV}$ satisfying the simultaneous equations of Equation 5 based on the projection function of the two different energy spectra and the energy value of the detected X-ray beam.

To this end, the line integral calculation unit 300 sets initial approximate values $E_L^{MV^0}$ and $E_H^{MV^0}$ of the energy values $E_L^{MV^n}$ and $E_H^{MV^n}$ as mean energy values of the energy spectra, respectively, as represented by Equation 6.

$$S_L(E_L^{MV^0}) = \frac{1}{|I|} \int S_L(E) dE, \qquad \text{<Equation 6>}$$

$$S_H(E_H^{MV^0}) = \frac{1}{|I|} \int S_H(E) dE$$

Here, Equation 6 can be obtained from Equation 4 by substituting 0 into parameters of $E_H^{MV}$ and $E_L^{MV}$ that is, $A_c$ and $A_p$, for the high and low energy spectra. The mean energy values of the energy spectra are values obtained by substituting 0 into $A_c$ and $A_p$, which are the parameters of $E_H^{MV}$ and $E_L^{MV}$, respectively.

In addition, the line integral calculation unit 300 calculates $E_L^{MV^n}$ and $E_H^{MV^n}$, which are the approximate values of the energy values satisfying the simultaneous equations of Equation 5, based on $A_c^n$ and $A_p^n$ which are first approximate values of the line integral values of the attenuation coefficients, and then calculates $A^{n+1}_c$ and $A^{n+1}_p$ which are second approximate values of the line integral values of the attenuation coefficients, based on $E_L^{MV^n}$ and $E_H^{MV^n}$ which are the approximate values of the energy values satisfying the simultaneous equations.

$E_L^{MV^n}$ and $E_H^{MV^n}$ can be calculated based on $A_c^n$ and $A_p^n$ by Equation 7.

$$-\ln\left(\frac{P_L}{|I|}\right) \approx -\ln S_L(E_L^{MV^n}) + A_c^n f_{KN}(E_L^{MV^n}) + A_p^n f_p(E_L^{MV^n}) \quad \langle\text{Equation 7}\rangle$$

$$-\ln\left(\frac{P_H}{|I|}\right) \approx -\ln S_H(E_H^{MV^n}) + A_c^n f_{KN}(E_H^{MV^n}) + A_p^n f_p(E_H^{MV^n})$$

Equation 7 can be obtained from Equation 4 by replacing the line integral values of the attenuation coefficients, that is, $A_c$ and $A_p$, with $A_c^n$ and $A_p^n$ which are the approximate values thereof.

In addition, $A_c^{n+1}$ and $A_p^{n+1}$ can be calculated based on $E_L^{MV^n}$ and $E_H^{MV^n}$ according to Equation 8.

$$\begin{bmatrix} A_c^{n+1} \\ A_p^{n+1} \end{bmatrix} = \frac{\begin{bmatrix} f_p(E_H^{MV^n}) & -f_p(E_L^{MV^n}) \\ -f_{KN}(E_H^{MV^n}) & f_{KN}(E_L^{MV^n}) \end{bmatrix} \begin{bmatrix} -\ln\left(\frac{P_L}{|I|}\right) + \ln S_L(E_L^{MV^n}) \\ -\ln\left(\frac{P_H}{|I|}\right) + \ln S_H(E_H^{MV^n}) \end{bmatrix}}{f_{KN}(E_L^{MV^n})f_p(E_H^{MV^n}) - f_{KN}(E_H^{MV^n})f_p(E_L^{MV^n})} \quad \langle\text{Equation 8}\rangle$$

Accordingly, the line integral calculation unit 300 may calculate $A_c^1$ and $A_p^1$, which are the approximate values of the line integral values of the attenuation coefficients, based on $E_L^{MV^0}$ and $E_H^{MV^0}$ which are initial approximate values of $E_L^{MV}$ and $E_H^{MV}$ satisfying Equation 5, calculate $E_L^{MV^1}$ and $E^{MV^1}_H$ based on $A_c^1$ and $A_p^1$, and calculate $A_c^2$ and $A_p^2$ based on $E_L^{MV^1}$ and $E_L^{MV^1} E^{MV^1}_H$.

In this way, the line integral calculation unit 300 can calculate the line integral values of the attenuation coefficients by obtaining the approximate values of the energy values satisfying Equation 5 and the approximate values of the line integral values of the attenuation values through repetition until the approximate values converge.

In other words, the line integral calculation unit 300 may calculate the approximate values of the line integral values of the attenuation values and the energy values satisfying Equation 5 when differences between the first approximate values $A_c^n$ and $A_p^n$, and the second approximate values $A^{n+1}_c$ and $A^{n+1}_p$ of the line integral values of the attenuation coefficients are less than or equal to preset limits.

In addition, when the differences between the first approximate values $A_c^n$ and $A_p^n$ and the second approximate values $A^{n+1}_c$ and $A^{n+1}_p$ of the line integral values of the attenuation coefficients exceed the preset limits, the line integral calculation unit 300 may replace the first approximate values $A_c^n$ and $A_p^n$ with the second approximate values $A^{n+1}_c$ and $A^{n+1}_p$ and may repeat the procedure of calculating the approximate values $E_L^{MV^n}$ and $E_H^{MV^n}$ of the energy values satisfying Equation 5 and the second approximate values $A^{n+1}_c$ and $A^{n+1}_p$ of the line integral values of the attenuation coefficients in the next stage according to Equations 7 and 8, as described above.

At this time, there can be at least one pair of energy values $E_L^{MV^n}$ and $E_H^{MV^n}$ satisfying Equation 7 within energy zone I.

In this case, the line integral calculation unit 300 selects one pair of energy values $E_L^{MV^n}$ and $E_H^{MV^n}$ satisfying Equation 7 to calculate the approximate values $A_c^{n-1}$ and $A_c^{n+1}$ of the line integral values of the attenuation coefficients in the next stage.

At this time, the line integral calculation unit 300 may select the lowest energy values among the energy values satisfying Equation 7 as the approximate values $E_L^{MV^n}$ and $E_H^{MV^n}$ of the energy values satisfying the simultaneous equations of Equation 5.

Alternatively, the line integral calculation unit 300 may select the highest energy values among the energy values satisfying Equation 7 as the approximate values $E_L^{MV^n}$ and $E_H^{MV^n}$ of the energy values satisfying the simultaneous equations of Equation 5.

When a small number of repetitions, for example, two or three repetitions, brings convergence of the attenuation coefficients, selection of the highest or lowest energy values from among the energy values satisfying Equation 7 does not provide an excessive burden of calculation.

However, with increasing number of repetitions, the line integral calculation unit 300 may select the approximate values $E_L^{MV^n}$ and $E_H^{MV^n}$ of the energy values satisfying the simultaneous equations of Equation 5 through calculation of the approximate values of the energy values satisfying Equation 7, thereby alleviating the burden of calculation.

In this case, assuming that $E_L^{MV^n}$ and $E_H^{MV^n}$ are functions of two variables with respect to pairs of real numbers and can be differentiated at an original point, linear functions of $E_L^{MV^n}$ and $E_H^{MV^n}$ can be approximately calculated by Equation 9 instead of Equation 7.

$$E_L^{MV^n}(A_c^n, A_p^n) = \quad \langle\text{Equation 9}\rangle$$

$$E_L^{MV^n}(0,0) + A_c^n \frac{\partial E_L^{MV^n}}{\partial x_1}(0,0) + A_p^n \frac{\partial E_L^{MV^n}}{\partial x_2}(0,0)$$

$$E_H^{MV^n}(A_c^n, A_p^n) =$$

$$E_H^{MV^n}(0,0) + A_c^n \frac{\partial E_H^{MV^n}}{\partial x_1}(0,0) + A_p^n \frac{\partial E_H^{MV^n}}{\partial x_2}(0,0)$$

FIG. 2 is a flowchart illustrating a method for computed tomography image processing in accordance with one embodiment of the present invention. Next, the method for computed tomography image processing according to the embodiment of the present invention will be described with reference to FIG. 2.

First, the X-ray detection unit 200 detects an X-ray beam emitted from the X-ray irradiation unit 100 and having passed through a subject, and outputs an energy value of the X-ray beam (S110).

Then, the line integral calculation unit 300 calculates a projection function represented by Equation 2 based on the detected energy value of the X-ray beam.

Here, the line integral calculation unit 300 calculates line integral values $A_c$ and $A_p$ of attenuation coefficients from the simultaneous equations of Equation 5 to calculate attenuation coefficients $a_c$ and $a_p$.

To this end, first, the line integral calculation unit 300 calculates approximate values of energy values satisfying the simultaneous equations of Equation 5 according to Equation 7 (S120).

That is, the line integral calculation unit 300 calculates $E_L^{MV^n}$ and $E_H^{MV^n}$, which are the approximate values of the energy values satisfying the simultaneous equations of Equation 5, based on $A_c^n$ and $A_p^n$ which are the first approximate values of the line integral values of the attenuation coefficients.

However, when operation S120 is conducted for the first time, that is, when n=0, the line integral calculation unit 300 sets initial approximate values $E_L^{MV^0}$ and $E_H^{MV^0}$ of the energy values, as described in Equation 6. In this case, the initial approximate values $E_L^{MV^0}$ and $E_H^{MV^0}$ of the energy values $E_L^{MV^n}$ and $E_H^{MV^n}$ are set as mean energy values of the energy spectra, respectively, as in Equation 6.

Then, the line integral calculation unit 300 calculates approximate values of the attenuation coefficients based on the approximate values of the energy values satisfying the simultaneous equations of Equation 5 according to Equation 8 (S130).

That is, the line integral calculation unit 300 may calculate the second approximate values $A_z^{n-1}$ and $A_z^{n+1}$ of the line integral values of the attenuation coefficients based on the approximate values $B_L^{MV^n}$ and $B_H^{MV^n}$ of the energy values satisfying the simultaneous equations.

Next, the line integral calculation unit 300 determines whether differences between the first approximate values and second approximate values of the line integral values of the attenuation coefficients are less than or equal to preset limits (S140).

If the differences between the first and second approximate values exceed the preset limits in S140, the line integral calculation unit 300 determines that the approximate values of the line integral values of the attenuation coefficients have not yet converged, and repeats calculation of the approximate values of the energy values satisfying Equation 5 (S120) and calculation of the approximate values of the line integral values of the attenuation values (S130) until the line integral values of the attenuation coefficients converge.

If the differences between the first and second approximate values are less than or equal to the preset limits in S140, the line integral calculation unit 300 determines that the approximate values of the line integral values of the attenuation coefficients have converged, and calculates the second approximate values as the line integral values of the attenuation coefficients (S150).

That is, the line integral calculation unit 300 calculates the second approximate values $A^{n+1}_c$ and $A^{n+1}_p$ of the line integral values of the attenuation coefficients as the line integral values $A_c$ and $A_p$ of the attenuation coefficients and calculates the attenuation coefficients $a_c$ and $a_p$ based on the line integral values $A_c$ and $A_p$ of the attenuation coefficients according to Equation 2.

Then, the image processing unit 400 reconstructs a tomogram based on the attenuation coefficients $a_c$ and $a_p$, which represent attenuation of the energy values of the X-ray beam, and terminates the process.

Here, the image processing unit 400 can reconstruct an accurate tomogram through calculation of the energy values of the X-ray beam passing through a subject based on the energy values of the X-ray beam measured by the X-ray detection unit 200 and the attenuation coefficients.

As such, according to the embodiments of the present invention, the apparatus and method for computed tomography image processing can calculate line integral values of attenuation coefficients constituting an integrand of an X-ray projection function using the mean value theorem for integrals in order to restore an image of a subject from X-ray beams detected in computed tomography image processing, thereby enabling efficient removal of artifacts from an X-ray tomogram while improving accuracy of the image through single X-ray irradiation without additional correction and repeated X-ray irradiation.

Although some embodiments have been disclosed above, it should be understood that these embodiments are given by way of illustration only, and that various modifications, variations, and alterations can be made without departing from the spirit and scope of the embodiments of the present invention. Therefore, the scope of the embodiments of the present invention should be limited only by the accompanying claims and equivalents thereof.

What is claimed is:

1. An apparatus for computed tomography image processing, comprising:
    an X-ray detector that detects an X-ray beam having passed through a subject and outputs an energy value thereof;
    a processor that calculates line integral values of attenuation coefficients representing attenuation of the energy value of the X-ray beam having passed through the subject and been detected, based on the energy value, and reconstructs a tomogram based on the line integral values; and
    a display that displays the tomogram;
    wherein the processor calculates, based on simultaneous equations obtained from a projection function of two different energy spectra and the energy value of the detected X-ray beam, line integral values of attenuation coefficients included in the projection function of the two different energy spectra and energy values satisfying the simultaneous equations;
    wherein the processor calculates approximate values of the energy values satisfying the simultaneous equations based on first approximate values of the line integral values of the attenuation coefficients, and calculates second approximate values of the line integral values of the attenuation coefficients based on the approximate values of the energy values satisfying the simultaneous equations;
    wherein the processor selects at least one of the lowest energy values and the highest energy values as the approximate values of the energy values satisfying the simultaneous equations, among energy values satisfying an equation in which the line integral values of the attenuation values in the simultaneous equations are replaced by the first approximate values of the line integral values of the attenuation values.

2. The apparatus for computed tomography image processing according to claim 1, wherein initial approximate values of the energy values satisfying the simultaneous equations are mean values of energy values of the two different energy spectra, respectively.

3. The apparatus for computed tomography image processing according to claim 1, wherein the processor calculates the line integral values of the attenuation coefficients and the approximate values of the energy values satisfying the simultaneous equations when differences between the first and second approximate values of the line integral values of the attenuation coefficients are less than or equal to preset limits.

4. The apparatus for computed tomography image processing according to claim 3, wherein the processor replaces the first approximate values of the line integral values of the attenuation coefficients by the second approximate values of the line integral values of the attenuation coefficients, and repeats a procedure of calculating the approximate values of the energy values satisfying the simultaneous equations and the second approximate values of the line integral values of the attenuation coefficients, when the differences between the first approximate values and the second approximate values of the line integral values of the attenuation coefficients exceed the preset limits.

5. A method for computed tomography image processing, comprising:
    detecting, by an X-ray detector, an X-ray beam emitted to a subject and outputting an energy value thereof;

calculating, by a processor, line integral values of attenuation coefficients representing attenuation of the energy value of the X-ray beam having passed through the subject and been detected, based on the energy value;

reconstructing, by the processor, a tomogram based on the line integral values; and displaying, by a display, the tomogram, wherein the processor calculates, based on simultaneous equations obtained from a projection function of two different energy spectra and the energy value of the detected X-ray beam, line integral values of attenuation coefficients included in the projection function of the two different energy spectra and energy values satisfying the simultaneous equations;

wherein calculating, by the processor, line integral values of attenuation coefficients comprises:

calculating approximate values of the energy values satisfying the simultaneous equations based on first approximate values of the line integral values of the attenuation coefficients, and calculating second approximate values of the line integral values of the attenuation coefficients based on the approximate values of the energy values satisfying the simultaneous equations, wherein, in calculation of the approximate values of the energy values satisfying the simultaneous equations, the processor selects at least one of the lowest energy values and the highest energy values as the approximate values of the energy values satisfying the simultaneous equations, among energy values satisfying an equation in which the line integral values of the attenuation values in the simultaneous equations are replaced by the first approximate values of the line integral values of the attenuation values.

6. The method for computed tomography image processing according to claim 5, further comprising:

initializing, by the processor, the approximate values of the energy values satisfying the simultaneous equations as mean values of energy values of the two different energy spectra, respectively.

7. The method for computed tomography image processing according to claim 5, wherein calculating, by the line integral calculation unit, line integral values of attenuation coefficients comprises:

calculating the line integral values of the attenuation coefficients and the approximate values of the energy values satisfying the simultaneous equations, when differences between the first and second approximate values of the line integral values of the attenuation coefficients are less than or equal to preset limits.

8. The method for computed tomography image processing according to claim 7, wherein calculating, by the processor, line integral values of attenuation coefficients comprises:

repeating a procedure of calculating the approximate values of the energy values satisfying the simultaneous equations and the second approximate values of the line integral values of the attenuation coefficients, when the differences between the first approximate values and the second approximate values of the line integral values of the attenuation coefficients exceed the preset limits.

* * * * *